United States Patent [19]

Taguchi et al.

[11] 4,272,781

[45] Jun. 9, 1981

[54] NONDESTRUCTIVE EXAMINING APPARATUS

[75] Inventors: Nobuo Taguchi, Fuchu; Tadashi Munakata, Tokyo; Yoshikata Kobayashi, Yokohama, all of Japan

[73] Assignee: Tokyo Shibaura Denki Kabushiki Kaisha, Tokyo, Japan

[21] Appl. No.: 72,592

[22] Filed: Sep. 5, 1979

[30] Foreign Application Priority Data

Sep. 8, 1978 [JP] Japan ................................. 53-109594
Jan. 17, 1979 [JP] Japan ................................. 54-3660[U]

[51] Int. Cl.³ ............................................. H04N 7/18
[52] U.S. Cl. .................... 358/100; 358/107; 358/108
[58] Field of Search .................. 358/100, 93, 96, 107, 358/108

[56] References Cited

U.S. PATENT DOCUMENTS

| 2,314,499 | 3/1943 | Howard | 358/96 |
|---|---|---|---|
| 2,891,339 | 6/1959 | Kao | 358/96 |
| 3,243,509 | 3/1966 | Stut | 358/107 |
| 3,930,942 | 1/1976 | Thome | 358/100 |
| 4,131,914 | 12/1978 | Bricmont | 358/100 |
| 4,194,218 | 3/1980 | Hasegawa | 358/100 |

Primary Examiner—Howard W. Britton
Attorney, Agent, or Firm—Stevens, Davis, Miller & Mosher

[57] ABSTRACT

The disclosed apparatus comprises a movable carriage on which an industrial television camera and nondestructive examining unit or probe are swingably supported. A control means for controlling the carriage, industrial television camera and the probe are also provided as is a monitor television for displaying the result of an examination made by the probe and a video tape recorder.

9 Claims, 29 Drawing Figures

NONDESTRUCTIVE EXAMINING APPARATUS

BACKGROUND OF THE INVENTION

This invention relates to a nondestructive examining apparatus.

With recent industrial development, high performance and high reliability are required by various machines and apparatus. For example, nuclear reactor containers are subjected to nondestructive examination not only during manufacturing but also during operation thereof. During the operation of a nuclear power plant due to the danger of radioactive radiation and during the machining of such narrow elements as nozzles, it is difficult for the operator to approach them. Moreover, from the standpoint of efficiency and safety, remote control and automation of the examining apparatus are highly desirable.

In pumping up stations too, due to the increase in the capacity of individual machines and the sites of installing the stations, demand for pump-turbines capable of operating under high heads is increasing. The configuration of the water flow path of a water wheel becomes extremely complicated for the purpose of minimizing the resistance of the flow path and maximizing the efficiency of the water wheel. Since the same water wheel is operated as either a pump or a turbine the cross-section of the flow path is becoming more complicated and narrow. Accordingly, development of a novel method and apparatus capable of accurately examining such complicated narrow portions without destroying them has been desired.

Figure 1:
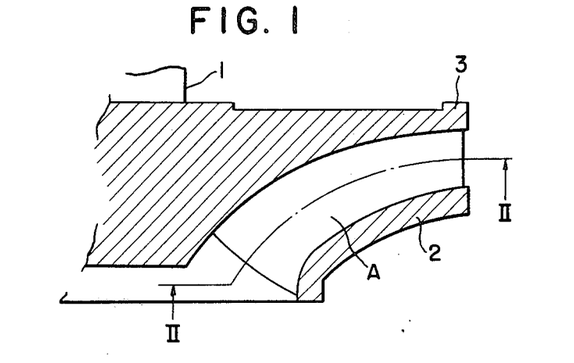
FIG. 1 is a longitudinal sectional view showing a portion of a runner of a pump-turbine to which the invention is applicable.
Figure 2:
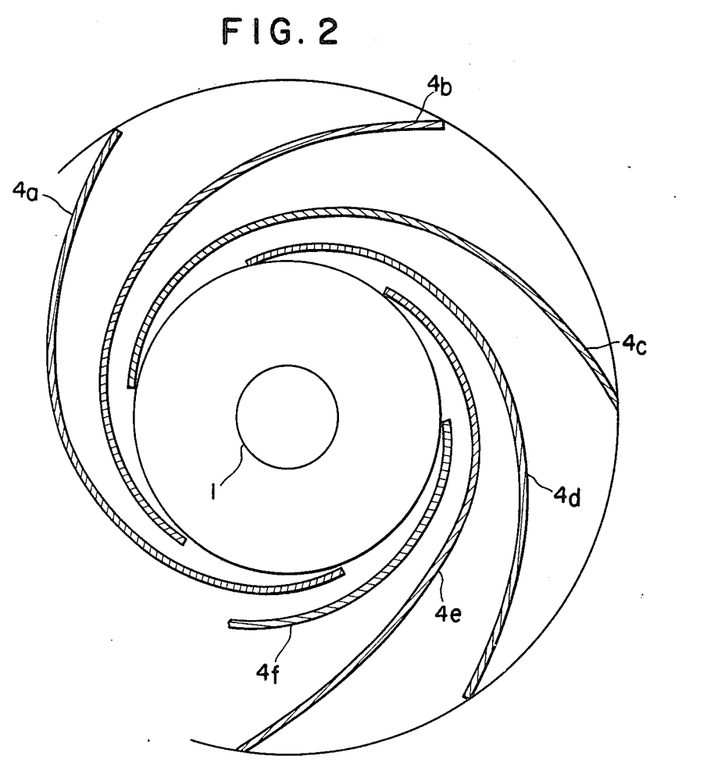
FIG. 2 is a cross-sectional view of the runner shown in FIG. 1 taken along the line II—II.

FIG. 1 shows a longitudinal cross-section of one example of the runner of a pump-turbine which rotates about a center shaft 1 and includes a plurality of water flow paths A, and FIG. 2 shows a cross-sectional view taken along a line II—II in FIG. 1. The nunner is made up of a shroud ring 2 and a crown plate 3 between which are provided a plurality of vanes $4_a$ through $4_f$. The flow paths defined by these vanes 4, the crown plate 3 and the shroud ring 2 are generally narrow and long and each vane extends spirally about one half about the periphery of the center shaft 1.

Figure 3A:
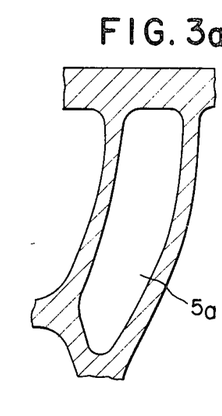
FIG. 3a, 3b and 3c are sectional views showing a variation in the cross-sectional configuration of the flow passageway of the runner.
Figure 3B:
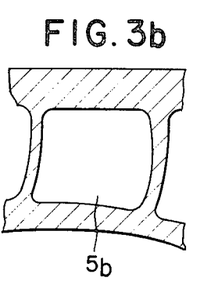
Figure 3C:
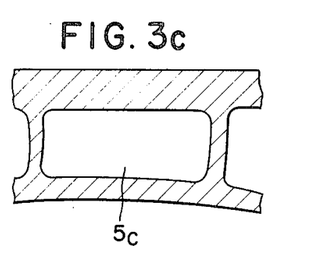

FIGS. 3a, 3b and 3c show cross-sectional views of the flow paths of the runner in which FIG. 3a shows a flow path $5_a$ near the shaft 1, FIG. 3b that of $5b$ at an intermediate portion, and FIG. 3c that of $5_c$ near the outer periphery of the runner. In a case of a pump-turbine having a capacity of 200–300 MVA, and operating under a head of 500–600 meters, the width of the flow paths changes from about 150 mm at $5_a$ to about 500 mm at $5_c$, while the height of the path varies from about 600 mm at $5_a$ to about 200 mm at $5_c$. Also the angle of each flow path varies continuously, and the length thereof amounts to about 4 m. Especially, in a hydroelectric power station, guide vanes and stationary vanes are disposed about the runner so that it is difficult to access the runner.

As the head and capacity of the pumping up station increase, the mechanical strength of the runner and the construction of the flow paths should be more vigorously controlled so that during manufacturing it is necessary to detect defects of the material and welds, and during running, at a definite interval, it is essential to detect or examine cracks caused by stresses, surface damage due to cavitation, and damage caused by gravel and sand contained in the water. In a prior art plant having a small capacity and operating under a low head, the operator can enter into the flow paths to perform such nondestructive examinations as penetration defect location and magnetic powder fault detection. However, in a large plant operating under a head of 500 to 60 meters, or 1000 meters, the operator cannot enter into the flow paths. Even if the operator can enter into the flow paths he must work under dangerous conditions so that development of a new type of nondestructive examining apparatus has been desired.

SUMMARY OF THE INVENTION

It is therefore an object of this invention to provide a novel nondestructive examining apparatus capable of examining narrow portions having complicated curved surfaces by remote control without destroying the portions being examined, and preserving the records of the examination.

Another object of this invention is to provide a novel nondestructive examining apparatus provided with an improved distance measuring device.

According to this invention there is provided nondestructive examining apparatus, characterized by comprising a carriage capable of running along a curved surface, an industrial television camera and a nondestructive examining unit which are swingably mounted on the carriage, control means for controlling the carriage, the industrial television camera and the nondestructive examining unit, and recording means including a video tape recorder for recording data produced by the nondestructive examining unit as a result of operation thereof, and video images produced by the industrial television camera.

According to another aspect of this invention, there is provided nondestructive examining apparatus characterized by comprising an industrial television camera carried by a carriage movable along a curved surface, the camera including means for changing a field of view, means for adjusting a focal length of the camera, and an illuminating camera; a monitor television for displaying image signals produced by the industrial television camera; means for inputting characters from outside; means for synthesizing data regarding a position of the field of view of the television camera, a position of the carriage, and a position of an arm swingably mounted on the carriage for supporting the indusrial television camera, the video signals and the inputted character to obtain a synthesized data, a monitor television for displaying the synthesized data, a nondestructive examining unit carried by the carriage to contact a surface to be examined; and means for recording picture images displayed on the monitor television and an output of the nondestructive examining unit.

DESCRIPTION OF THE PREFERRED EMBODIMENT

Figure 4:
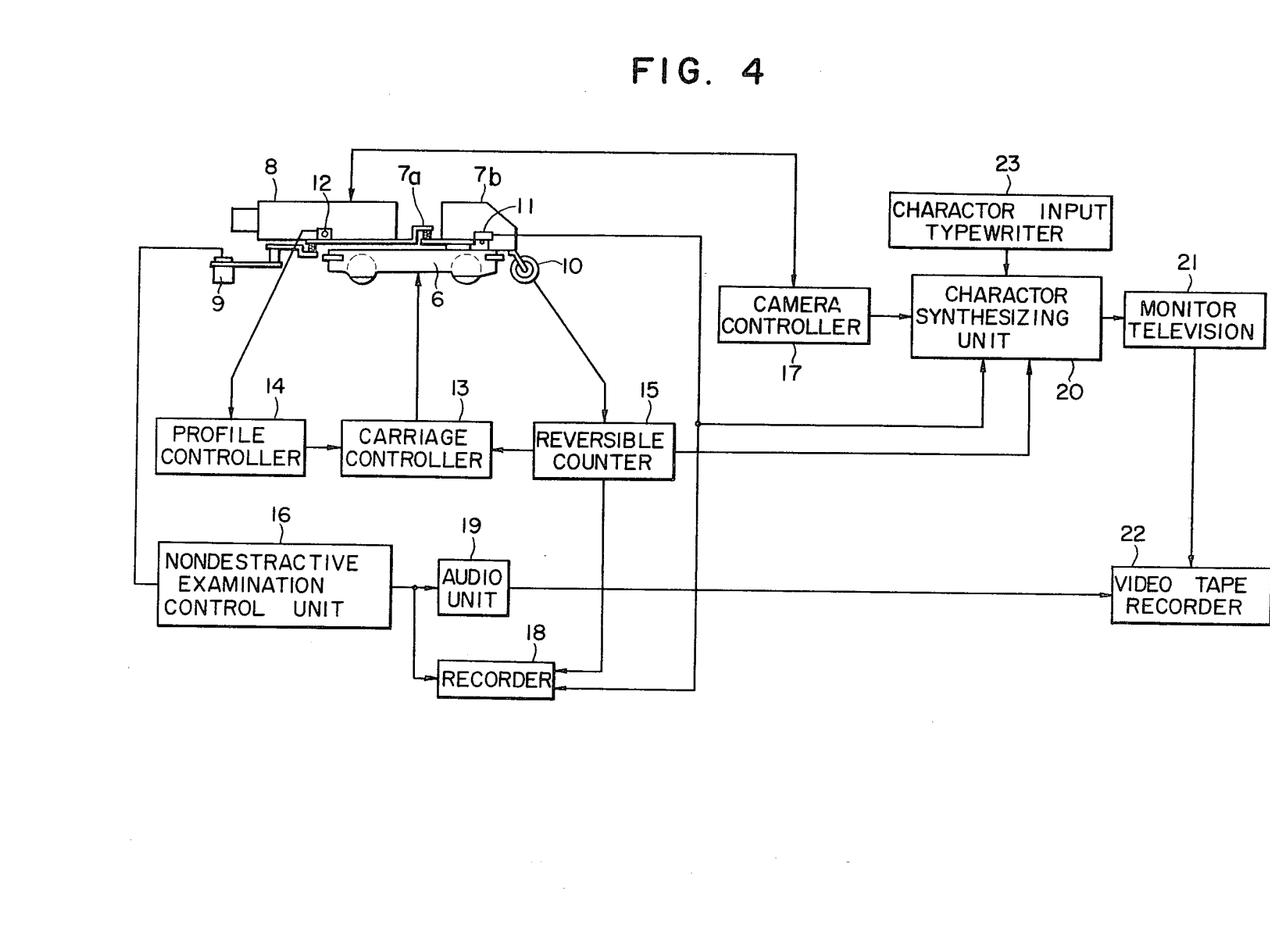
FIG. 4 is a block diagram showing the construction of the nondestructive examining apparatus of this invention.

As diagrammatically shown in FIG. 4, the nondestructive examining apparatus of this invention comprises a carriage 6 constructed to run along narrow portions having complicated curved surfaces, an arm $7_a$ and arm driving mechanism $7_b$ mounted on the carriage 6 free to move, an industrial television (ITV) camera 8 mounted on the arm $7_a$, a nondestructive examining unit 9 swingably mounted on the outer end of the arm $7_a$, a distance measuring device 10 mounted on the rear end of the carriage 6, an angle detector 11 displaying the angle of the arm, and a detector 12 for profile controlling the arm to move along the wall surfaces of the narrow portions, a carriage controller 13 for controlling the carriage, a profile controller 14 for controlling the arm to effect profiling and a presetable reversible counter 15 for controlling the carriage controller 13 in response to the output signal from the distance measuring device 10. There are also provided a nondestructive examination control unit 16 which applies a signal to the probe of the nondestructive examining unit 9 to detect presence or absence of a defect, and a camera controller 17 which controls the industrial television camera 8. The output of the nondestructive examination control unit 16 is applied to a recorder 18, and to an audio unit 19 which converts the output into a voice output, whereas the output of the camera controller 17 is connected to a character synthesizer 20, the output thereof being supplied to a monitor television 21 and a video tape recorder 22 which records and preserves the images displayed on the monitor television 21. There is further provided a character input typewriter 23 which facilitates later collation of the preserved contents.

Figure 5:
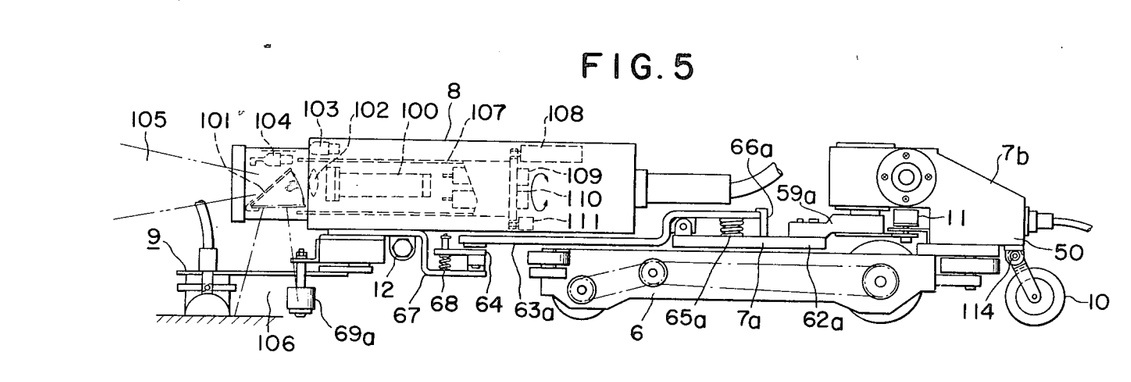
FIG. 5 is a side view showing one embodiment of the nondestructive examining apparatus of this invention.
Figure 6:
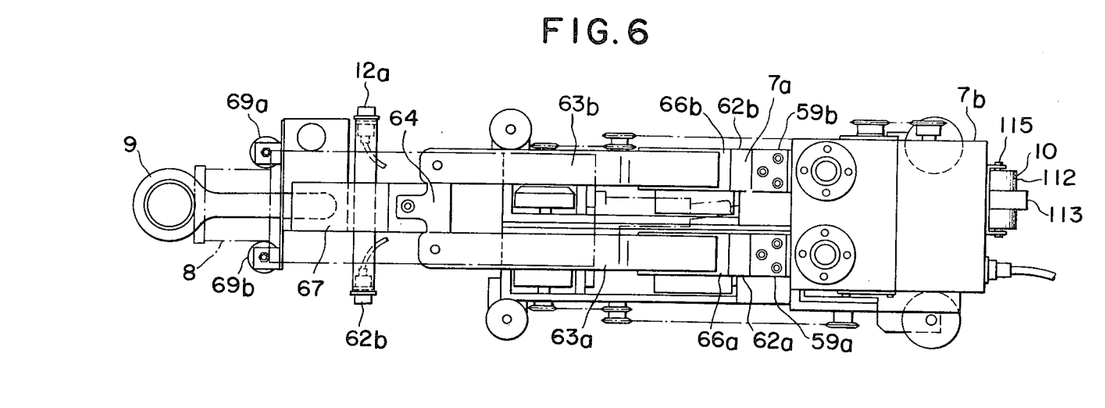
FIG. 6 is a plan view thereof.
Figure 7:
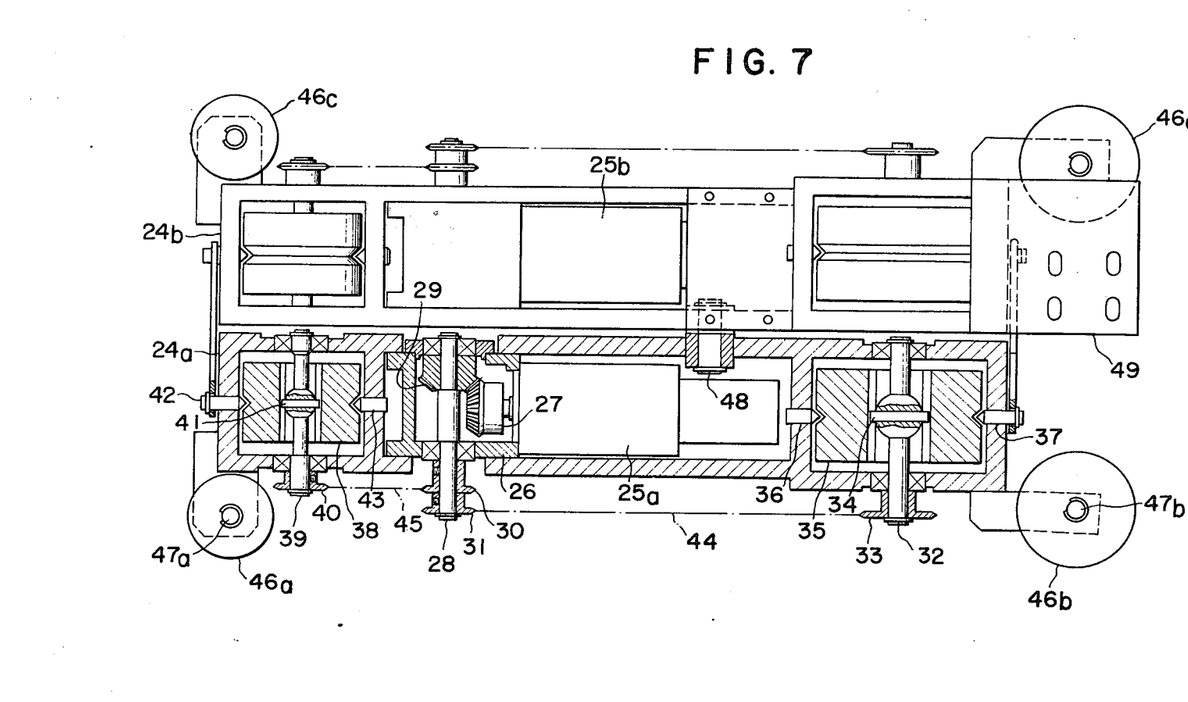
FIG. 7 is a plan view showing a carriage utilized in this invention, with a portion shown in section.

With reference now to FIGS. 5, 6 and 7, the construction of the carriage 6 will firstly be described. As shown in these figures, a gear box 26 containing a motor $25_a$ with a reduction gearing is mounted on a frame $24_a$ and a bevel gear 27 is mounted on the shaft of the motor $25_a$ to mesh with a bevel gear 29 secured to a shaft 28 which is rotatably supported in gear box 26 by radial and thrust bearings. Sprocket wheels 30 and 31 are secured to one end of the shaft 28. Furthermore, a shaft 32 is rotatably supported by the frame $24_a$ through radial and thrust bearings and a sprocket wheel 33 is secured to one end of the shaft 32.

Figure 8:
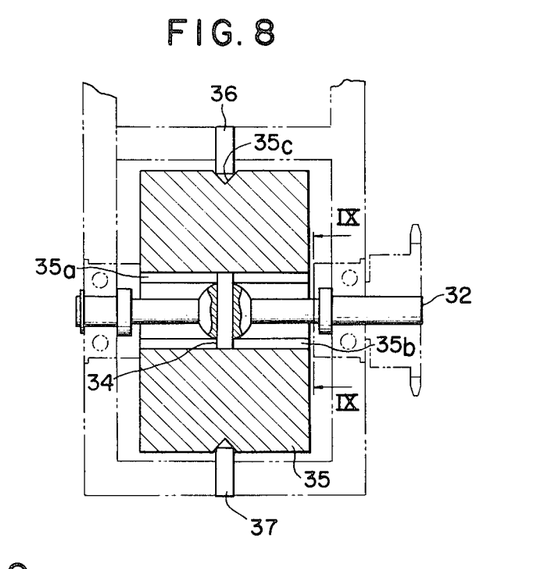
FIG. 8 is a sectional view showing a magnet roller utilized in the apparatus of this invention.
Figure 9:
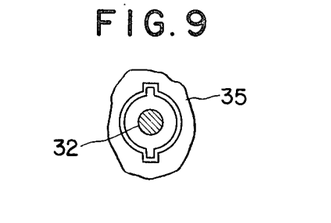
FIG. 9 is a cross-sectional view of a portion of the magnet roller shown in FIG. 8 taken along a line IX—IX thereof.

As best shown in FIGS. 8 and 9, a cross pin 34 extends through the central portion of the shaft 32 with both ends received in two axial key grooves $35_a$ and $35_b$ provided for the central bore of the magnet roller 35. The magnet roller 35 is formed with a circumferential V-shaped groove $35_c$ for slidably receiving pins 36 and 37 secured to the frame $24_a$. The axes of the pins 36 and 37 are coaxial and intersect at right angles with the axis of shaft 32. The central portion of the shaft 32 through which the cross-pin 34 extends is spherical.

Magnet roller 38, shaft 39, sprocket wheel 40, and pins 41, 42 and 43 have the same construction as magnet roller 35, shaft 32, sprocket wheel 33 and pins 34, 37 and 36 described above. Sprocket wheels 31 and 33 are coupled together by an endless chain. Similarly, sprocket wheels 30 and 40 are also coupled together through an endless chain 45. Rollers $46_a$ and $46_b$ are rotatably mounted on shafts $47_a$ and $47_b$ respectively.

Similar elements are also mounted on a frame $24_b$ and a stub shaft 48 extends through opposing sides of the frames $24_a$ and $24_b$ so as to permit relative rotation of the frames $24_a$ and $24_b$ about the stub shaft 48. A base 49 for supporting arm driving mechanism is mounted on the frame $24_b$.

Figure 10:
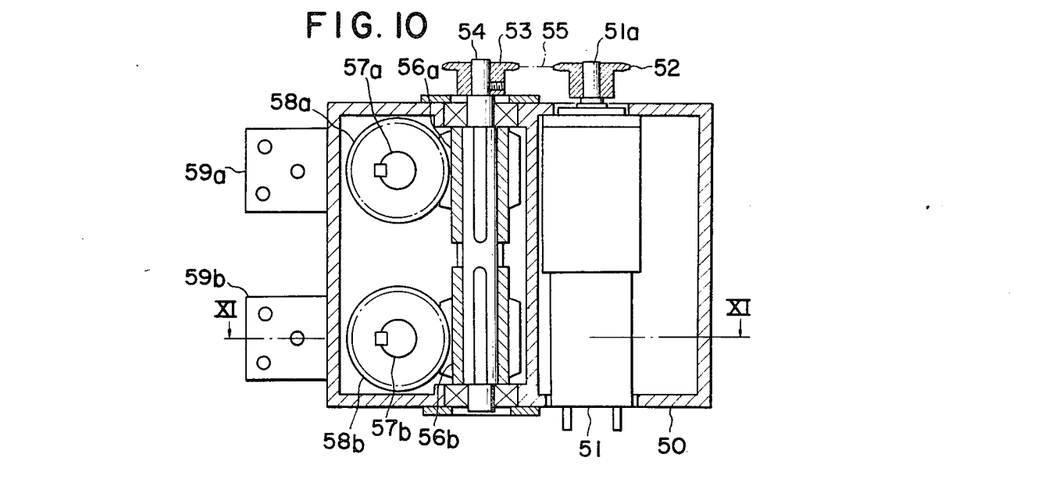
FIG. 10 is a partial view, partly in section, showing the arm driving mechanism utilized in the apparatus of this invention.
Figure 11:
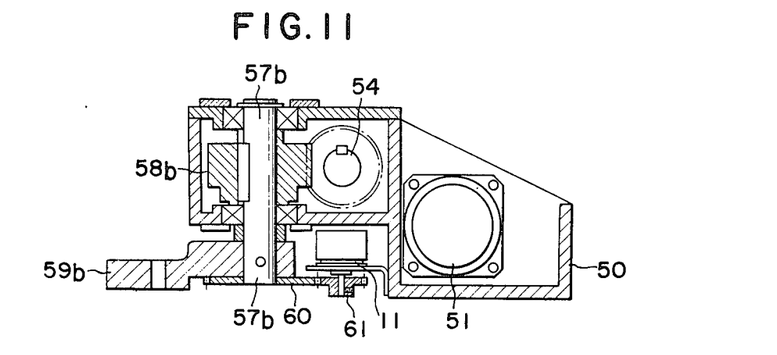
FIG. 11 is a sectional view taken along a line XI—XI shown in FIG. 10.

The arm driving mechanism $7_b$ will now be described. As shown in FIGS. 5 and 6, this mechanism is secured to the base 49 of the carriage 6. FIGS. 10 and 11 show a plan view and a side view of the arm driving mechanism $7_b$ respectively. As shown, a sprocket wheel 52 is mounted on the output shaft $51_a$ of a geared motor 51 contained in a gear box 50, and a sprocket wheel 53 is secured to one end of a shaft 54 with both ends journalled by radial and thrust bearings. The sprocket wheels 52 and 53 are coupled together through an endless chain 55. Worms $56_a$ and $56_b$ are secured to shaft 54 to mesh worm wheels $58_a$ and $58_b$ respectively secured to shafts $57_a$ and $57_b$. These shafts are journalled by radial and thrust bearings and their one ends project through the gear box 50 to support bases $59_a$ and $59_b$ respectively as shown in FIG. 10. A gear 60 is secured to one end shaft $57_b$ to mesh with a gear 61 secured to a shaft for rotating the swing angle detector 11.

The distance measuring device 10 (see FIG. 6) connected to the gear box 50 through a pin joint 114 comprises an outer rotating type pulse oscillator 112 and a magnet roller 113 secured to surround the oscillator. The arm $7_a$ comprises members $62_a$ and $62_b$ respectively connected to the bases $59_a$ and $59_b$ projecting outwardly from the arm driving mechanism $7_b$, a pair of members $63_a$ and $63_b$ secured to members $62_a$ and $62_b$ and a member 64 connected to the outer ends of the members $63_a$ and $63_b$ through pin joints, these members constituting a parallelogram. Members $62_a$ and $63_a$ are connected together through a compression spring $65_a$ and a stop member $66_a$, whereas members $62_b$ and $63_b$ are interconnected by a compression spring $65_b$ and a stop member $66_b$ so as to form a pin joint permitting swinging in only one direction. The member 64 at the outer end of the arm $7_a$ rotatably supports a mounting plate 67 through a pin joint, the mounting plate 67 being biased in one direction by a compression spring 68. At the outer end of the mounting plate 67 are mounted spherical wheels $69_a$ and $69_b$ (see FIG. 5) by a supporting pin to be rotatable in any direction. Profile sensors $12_a$ and $12_b$ are mounted on both sides of the mounting plate 67. The industrial television camera 8 and the nondestructive examining unit 9 are also mounted on the mounting plate 67.

Figure 12:
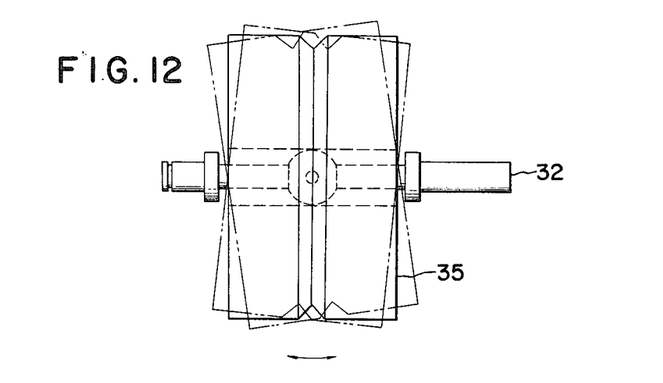
FIG. 12 is a diagrammatic representation useful to explain the operation of the magnet roller shown in FIG. 8.

The operation of the nondestructive examining apparatus of this invention will now be described. The torque of the geared motor $25_a$ contained in the gear box 26 is transmitted through bevel gears 27 and 29 to rotate the sprocket wheels 30 and 31 mounted on the outer end of shaft 28. The torque is further transmitted to the sprocket wheels 33 and 40 through chains 44 and 45 to rotate shafts 32 and 39, thereby rotating magnet rollers 35 and 38 through pins 34 and 41. As shown in FIG. 12, the magnet roller 35 is rotatable about coaxial pins 36 and 37. Further, as shown in FIGS. 8 and 9, since the pin 34 can slide along key grooves $35_a$ and $35_b$ of the magnet roller 35, even when the rolling surface of the magnet roller 35 is not parallel with shaft 32, the magnetic roller can roll along a body to be examined in an intimate contacting condition. To ensure adhesion of the magnet roller, the surface of the body should be made of magnetic material (this condition should be fulfilled for another three magnet rollers).

Figure 13A:
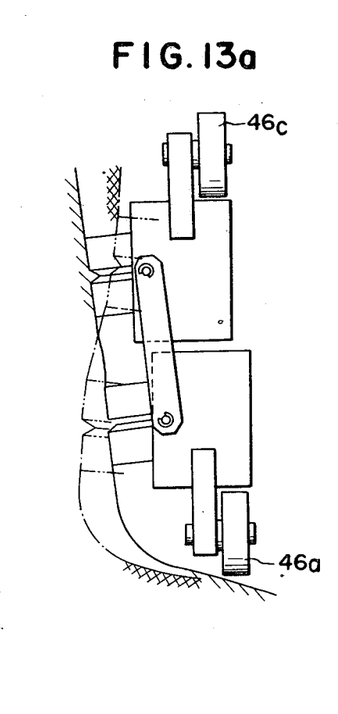
FIGS. 13a, 13b and 13c are side views showing different running states of the carriage.
Figure 13B:
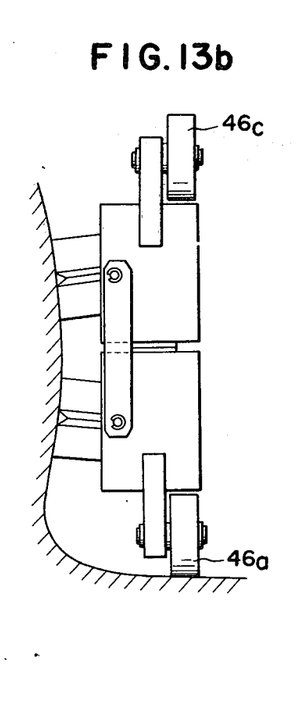
Figure 13C:
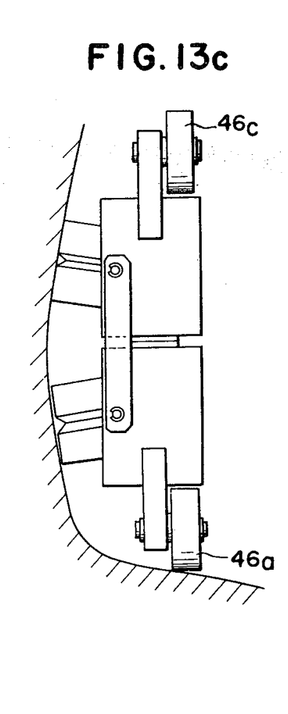

FIGS. $13a$, $13b$ and $13c$ show the intimate contact relationship between the magnet roller and the surface along which the roller rolls (hereinafter termed a running surface) even when the running surface is irregular. Since the frames $24_a$ and $24_b$ are rotatable about pin 48, even when the running surface is skewed as shown in FIG. $13a$. four magnet rollers can run without disengaging the running surface. When four magnet rollers run along the wall surface, the rollers $46_a$ and $46_b$ mounted on the frames $24_a$ and $24_b$ are brought into contact with a bottom wall surface so that they can smoothly run along corners. In the condition shown in FIGS. $13a$–$13c$, rollers $46_a$ and $46_b$ contact the bottom surface, but when the apparatus passes along upper corners, the rollers $46_c$ and $46_d$ would engage the upper wall surface.

The operation of the arm driving mechanism will now be described. Thus, the torque of the motor 51 rotates sprocket wheels 52 and 53, shaft 54, worms $56_a$ and $56_b$, worm wheels $58_a$ and $58_b$ and shafts $57_a$ and $57_b$ to swing the bases $59_a$ and $59_b$. The rotation of the shaft $57_b$ rotates the angle detector 11 through gears 60 and 61 to swing bases $59_a$ and $59_b$.

The distance measuring device 10 takes the form of an outer rotating type pulse generator and can follow the irregularity of the running surface because it is caused to adhere to the running surface by magnet roller 113 and supported by a pin joint 114 thereby accurately measuring the running distance. Supply of operating power and transmission and receival of signals are performed through wires contained in the central shaft 115 and its output is supplied to the reversible counter 15, as will be described later.

Since the arm mounted on the bases $59_a$ and $59_b$ comprises a parallelogram, the industrial television camera 8 and the nondestructive examining unit 9 are maintained in a definite direction irrespective of the swinging of the arm. Thus, the industrial television camera 8 can always supervise a definite direction.

Figure 14A:
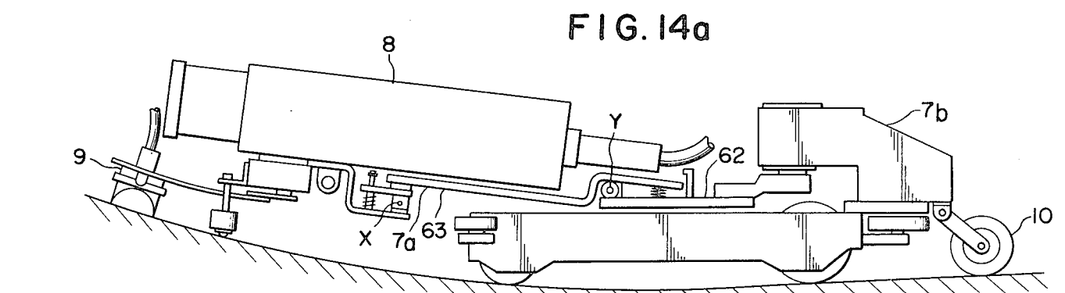
FIGS. 14a and 14b are side views showing different running states of the nondestructive examining apparatus of this invention.
Figure 14B:
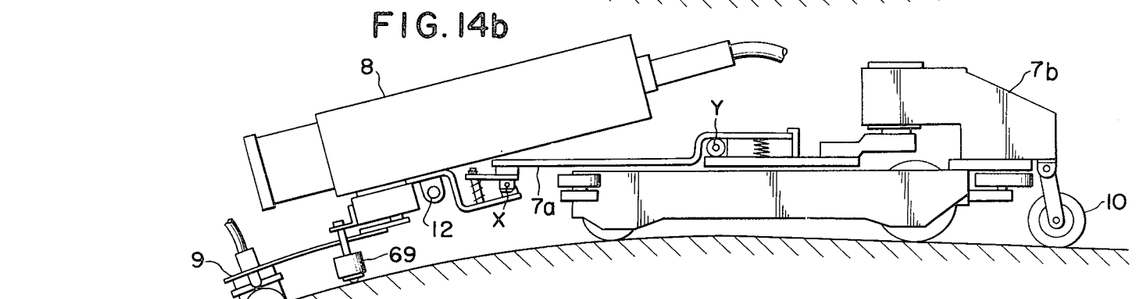

In FIG. $14a$ the running surface of the magnet roller is concave in the direction of running, whereas in FIG. $14b$ the running surface is convex. Regardless of the concave or convex configuration, the spherical wheels $69_a$ and $69_b$ are held in intimate contact with the running surface by compression springs $65_a$, $65_b$ or 68. In the case of a concave running surface, the profiling is done with axis Y as an articulation, whereas in the case of a convex running surface, axis X is used as the articulation. For this reason, the industrial television camera 8 and the nondestructive examining unit 9 are maintained at a constant distance from the running surface.

Figure 15:
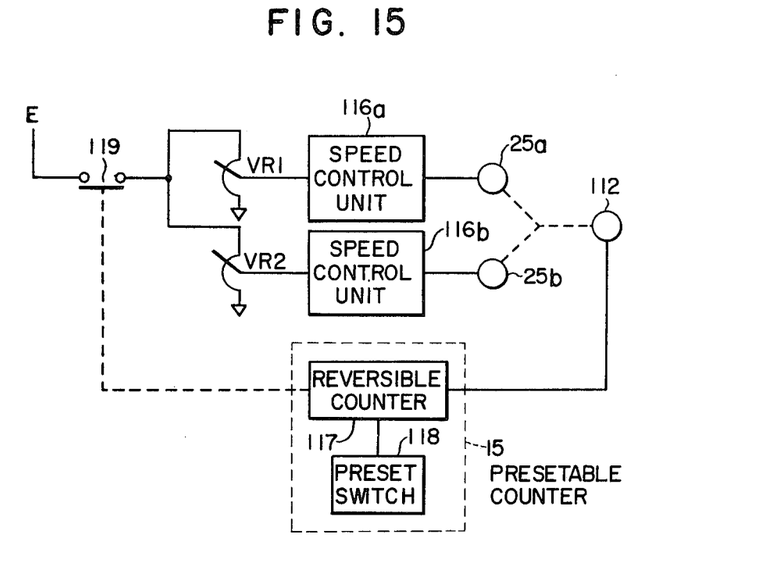
FIG. 15 is a connection diagram showing the control circuit of the carriage.

The control of the carriage 6 will now be described with reference to FIG. 15. As shown, geared motors $25_a$ and $25_b$ are driven by speed control units $116_a$ and $116_b$ respectively which are controlled by resistors VR1 and VR2. Thus, where instructions given by these resistors are equal, the motors $25_a$ and $25_b$ rotate at the same speed thus advancing the carriage straightforwardly. However, where the instructions issued by two resistors VR1 and VR2 are not equal, both motors rotate at different speeds so that the carriage 6 revolves with the outer wheel rotating at a lower speed as the inner wheel. A pulse generator 112 representing the running distance is of the reversible detection type. For example, when the rate of pulse generation is set to generate one pulse per one mm, pulses of a number corresponding to the distance from a reference point (the initial position of the carriage is taken as 0) are inputted to the reversible counter 117 to perform an addition operation where the carriage is advanced in accordance with the instructions given by resistors VR1 and VR2, or a subtraction operation when the carriage is retracted, whereby the reversible counter 117 counts the running distance in terms of mm units. Where a preset switch 118 for the presettable counter 15 is set to a desired value (distance) from the reference point, as the count of the reversible counter 117 becomes equal to the preset value, contact 119 is opened by the output signal. Thus, when the count of the reversible counter 117 does coincide with the preset value, contact 119 is closed to connect resistors VR1 and VR2 to a source E. When the count coincides with the preset value, the resistors VR1 and VR2 are disconnected from the source thus stopping both motors $25_a$ and $25_b$. In this manner, by the presetting of the reversible counter the carriage can be stopped at any desired position.

Figure 16:
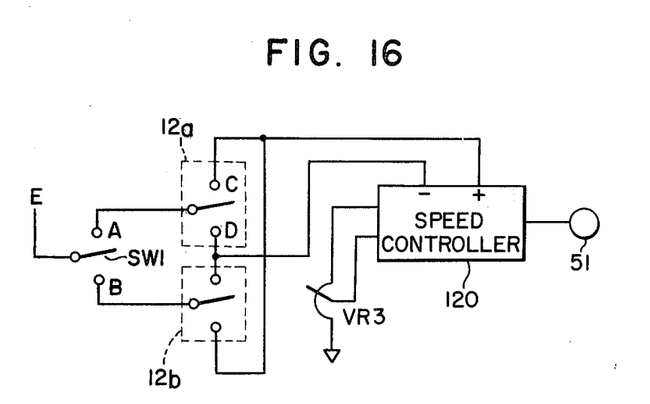
FIG. 16 is a connection diagram showing the control circuit for controlling profiling action of the arm.

The profile controller 14 for controlling the arm will now be described with reference to FIG. 16. Thus, a motor 51 with a speed reduction gearing is controlled by a variable resistor VR3 connected to a speed control circuit 120 for varying the speed. The speed control 120 is provided with terminals (+) and (−) for receiving signals to reverse the direction of rotation of the motor 51. Where profile detectors 12$_a$ and 12$_b$ are used, a switch SW1 is thrown to the upper contact A to supply power to detector 12$_a$ from source E. Where the carriage is run with the arm maintained at any angle, the distances from the upper and lower wall surfaces of the narrow flow passage vary from time to time. When the detector 12$_a$ does not contact to the upper wall surface, the switch of the detector 12$_a$ would be thrown to the upper contact C to supply the power to the positive terminal (+) of the speed control circuit so that the motor 51 rotates under a command given by variable resistor VR3 to raise the arm. When the arm rises to bring the detector 12$_a$ into contact with the upper wall surface, the switch of the detector 12$_a$ would be thrown to the lower contact D so as to reverse the rotation of the motor 51 to lower the arm. In this manner the arm can profile the upper wall surface. When the switch SW1 is thrown to the lower contact D the profile detector for the lower wall surface operates to perform similar profiling operation. Where a profiling operation is not necessary an external switch, not shown, is connected to the positive and negative terminals to move the arm to a desired position by the cooperation of the external switch and the variable resistor. At this time, the angle of the arm is displayed by the angle detector 11.

Figure 17:
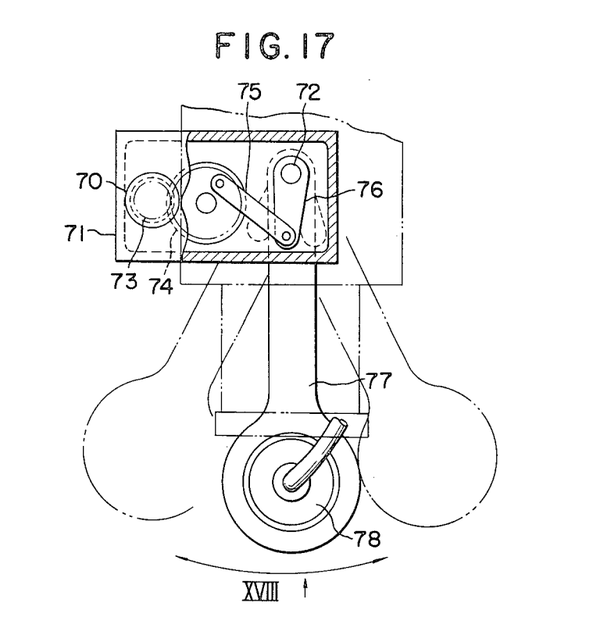
FIG. 17 is a plan view showing the supporting mechanism of the nondestructive examining apparatus of this invention.
Figure 18:
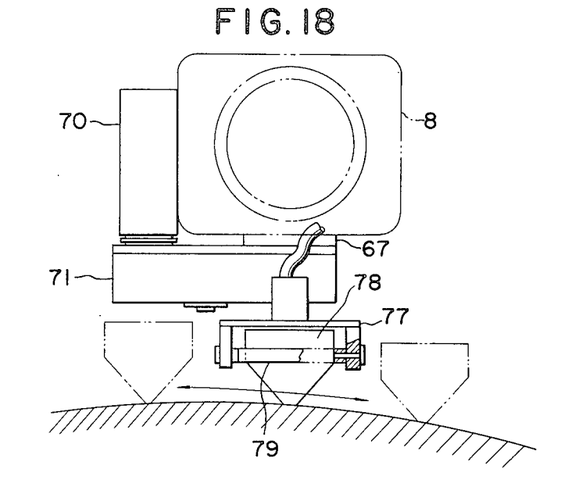
FIG. 18 is a front view, partly in section of the supporting mechanism shown in FIG. 17 taken along a line XVIII.

The nondestructive examining unit 9 will now be described. FIGS. 17 and 18 show a plan view and a front view respectively of a nondestructive examining unit for examining a flat portion. When a geared motor 70 rotates, the output shaft 72 of a gear box 71 swings the examining unit via gears 73, 74, a link 75 and a crank lever 76. A leaf spring 77 is connected to the output shaft 72, and an annular member 79 for holding a probe 78 is connected to the outer end of the leaf spring through a pin.

Figures 19A, 19B, 20:
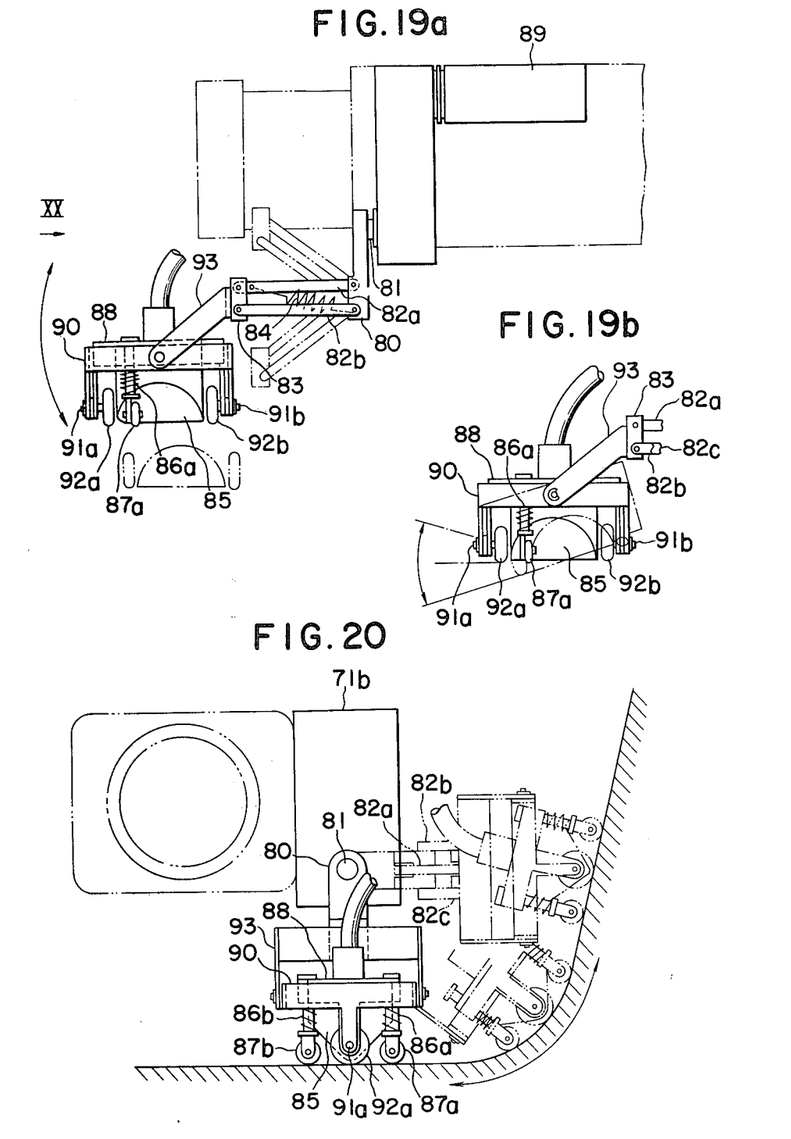
FIGS. 19a and 19b are side views showing another supporting mechanism of the nondestructive examining apparatus of this invention.
FIG. 20 is a side view of the supporting mechanism shown in FIG. 19 as seen in the direction of arrow XX.

FIGS. 19$a$, 19$b$ and 20 show a nondestructive examining unit for examining corner portions. Again, the output shaft 81 swings the examining unit through an arm 80 and a similar mechanism. More particularly, three links 82$_a$, 82$_b$ and 82$_c$ are connected to the lower end of the arm through connecting pins, and a supporting plate 83 is connected to the other ends of these links through connecting pins. Thus, links 82$_a$, 82$_b$ and 82$_c$ and the supporting plate 83 constitute a parallelogram which is biased in one direction by a coil spring 84. An inner cylinder 88 for holding a probe 85 provided with a pair of auxiliary wheels 87$_a$ and 87$_b$ which are urged by compression springs 86$_a$ and 86$_b$ respectively so as to freely extend and contact is tiltably connected to an outer cylinder 90 through pins 89$_a$ and 89$_b$. Wheels 92$_a$ and 92$_b$ are rotatably mounted on the inner ends of pins 91$_a$ and 91$_b$. The outer cylinder 90 is connected by connecting pins to a U-shaped supporting arm 93 secured to the supporting plate 83 such that the outer cylinder 90 can freely swing in a direction perpendicular to the relative direction of swinging between the inner cylinder 88 and the outer cylinder 90. The two types of the nondestructive examining units described above are used in the following manner. To examine a flat portion, the nondestructive examining unit 9 is mounted on the surface of the supporting plate 67 secured to one end of the arm 9 which confronts the surface to be examined, as shown in FIGS. 17 and 18. The probe 78 which is supported to always follow the irregularity of the surface to be examined by the resiliency of the leaf spring 77 and the connecting pin provided for the annular member 79 scans the surface being examined as shown by arrows in FIGS. 17 and 18. At this time, when the carriage 6 is advanced or retracted at a constant speed the probe 78 is caused to move along a serpentine path on the surface being examined to examine a stripe shaped region. Further, when the arm 7$_a$ is repeatedly swung, the surface can be examined over a wide area without being limited to the locus of running of the carriage 6.

To examine a corner portion, the nondestructive examining unit 9 is mounted on the side of the industrial television camera 8, as shown in FIGS. 19$a$, 19$b$ and 20. As arm 7$_a$ is swung to bring the nondestructive examining unit 9 near a corner portion and when the motor 89$_a$ is rotated, the supporting member 80 is swung. At this time, the free end of the unit 9 is urged to a portion to be examined by the action of the parallelogram links 82$_a$, 82$_b$ and 82$_c$ and the coil spring 84, and the wheels 92$_a$ and 92$_b$ are caused to follow the irregular surface being examined by the connecting pins between supporting arms 93 secured to the supporting plate 83 at the fore ends of the links and the outer cylinder 90. The inner cylinder 88 holding the probe 85 is caused to swing about pins 91$_a$ and 91$_b$ to be always normal to the surface being examined by coil springs 86$_a$ and 86$_b$ provided for the pair of auxiliary wheels 92$_a$ and 92$_b$. Consequently, as the supporting member 80 is swung the probe 85 would be moved as shown by dot and dash lines shown in FIG. 20. When the carriage 6 is moved forwardly or backwardly in the same manner as in the case of a flat surface, the probe 85 is moved sinuously passed the corner portion to examine a stripe shaped region including the corner. To examine a corner on the opposite side the nondestructive examining unit 9 is mounted on the opposite side of the industrial television camera 8.

Figure 21:
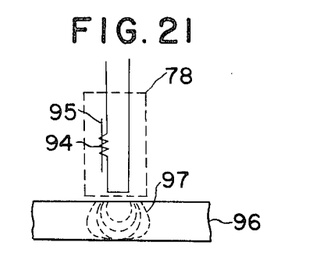
FIG. 21 is a view for explaining the operation of an eddy current probe.

A modified method of nondestructive examination of a flat portion by utilizing eddy current will now be described. In this case, as shown in FIG. 21, a probe 78 is formed by a coil 94 and a core 95 so that the coil 94 is energized by alternating current, and the coil produces AC magnetic flux to induce eddy current 97 in a member 96 adjacent to the coil. The eddy current flows not only through the surface but also through the interior of the member 96 to produce secondary magnetic flux in the direction opposite to that of the original flux. These fluxes are used to represent electrical and physical characteristics of the member 96.

Figure 22:
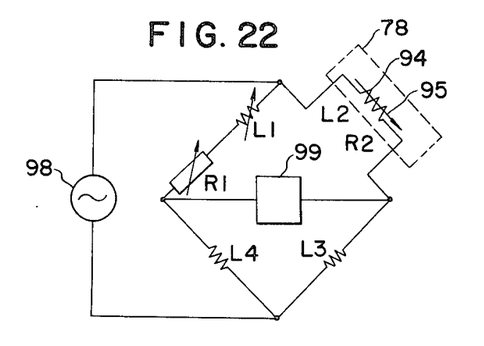
FIG. 22 is a connection diagram of the eddy current probe.

The nondestructive examination controller 16 which controls the coil 94 of the probe 78 comprises an AC bridge circuit shown in FIG. 22. The circuit comprises an AC source 98, inductors $L_1$, $L_2$, $L_3$ and $L_4$ and resistors $R_1$ and $R_2$ and the output of a detector 99 is zero when the bridge circuit is at a balanced condition. At first, the probe 78 is mounted on a sample free from any defect to balance the bridge circuit by adjusting the variable inductor $L_1$ and the variable resistor $R_1$. When there is a defect in the path of the eddy current in the sample, the impedances $L_2$ and $R_2$ of coil 94 change to cause unbalance of the bridge circuit thereby producing an output of the detector 99. The optimum frequency of the AC source 98 is determined in accordance with the material of the sample so that when the probe 78 is swung at a definite distance from the sample, flaws and defects within the range of swinging of the probe can be detected. By swinging the probe 78 while running the carriage 6, a nondestructive examination of a flat surface can be made automatically. By applying the output of the detector 99, the output of the reversible counter 15 representing the running distance and the output of the detector 11 representing the angle of the arm to a recording meter, it is possible to readily judge the position of defects and the condition thereof.

The industrial television camera 8 mounted on the supporting plate 67 at the end of arm $7_a$ is contracted to change the direction of field of view, to rotate the field and to adjust its focal length. When the carriage is advanced through flow passages $5_a$, $5_b$ and $5_c$ shown in FIGS. $3_a$, $3_b$ and $3_c$, a lamp 103 in the camera 8 is lighted and the forward view is adjusted by inclining a reflective mirror 101 by a motor 110 (see FIG. 5). The movement of the carriage is controlled by an operator while viewing the monitor television 21 (FIG. 4). At a position where the signal produced by the nondestructive examining unit 9 is normal or abnormal the carriage 10 is stopped and the reflective mirror 101 is inclined 45° by motor 110 to change the field of view from 105 to 106. This permits examination of the wall surfaces of the flow passages $5_a$, $5_b$ and $5_c$ and the defects of the wall surface are picked up by the image pickup tube 100 and displayed on the monitor television 21. Of course, at this time, lamp 104 is lighted to illuminate the wall surfaces. To inspect the entire peripheral surface, a light receiving unit 107 including a lens 102 and the reflective mirror 101 is rotated by motor 108. The industrial television camera is also constructed such that for the purpose of compensating for the switching between the forward field of view 105 and the lateral field of view 106 as well as the distance to the wall surface the image pickup tube 100 is moved by motor 109 to adjust its focal length. The control of motors 108, 109 and 110 and the switching between lamps 103 and 104 are effected by the camera controller 17 shown in FIG. 4. The video signals produced by the image pickup tube 100 are also controlled by the camera controller 17 and then displayed on the monitor television 21 via character synthesizing unit 20. The image of the monitor television is recorded by a video tape recorder 22 and for the convenience of later use necessary data such as dates and examined portions are also recorded. The output of a detector 111 which detects the angular position of the light receiving unit 107, the output of the distance measuring device 10 and the output of the detector 11 representng the angle of the arm are synthesized by the character synthesizing unit 20. Accordingly, all data including the position on the wall surface, the field of view of the industrial television camera, the data, location and the identification number of the machine are displayed simultaneously on the monitor television and recorded by the video tape recorder 22. The output of the nondestructive examining unit 9 is applied to an audio unit 19 via the control unit 16 and connected into sound which is also recorded by the video tape recorder 22. The audio unit 19 does not produce any sound when the AC bridge circuit is in a balanced condition at the time of eddy current test or under a normal condition but produces sound because the bridge circuit becomes unbalanced in the presence of a defect. As the volume of the sound is proportional to the size of the defect, an operator who listens to the sound reproduced from the video tape recorder can readily determine whether he should carefully observe the displayed image or keep stationary the image. To enable more detailed examination of the defect it is possible to magnify the image of the defect by the camera controller 17.

The data recorded by the video tape recorder can also be used for the examination of a machine during manufacture, for the seasonal inspection during operation and for the analysis of an abnormal condition. The output of the eddy current fault detector can also be recorded by the video tape recorder as numerical data. The running and stoppage of the carriage can also be controlled by a program control through a positional servo system, a command signal from the character input typewriter or data recorded in the video tape recorder in addition to a control effected by a presettable reversible counter. It is also possible to bring the carriage back to the defect.

Figure 23:
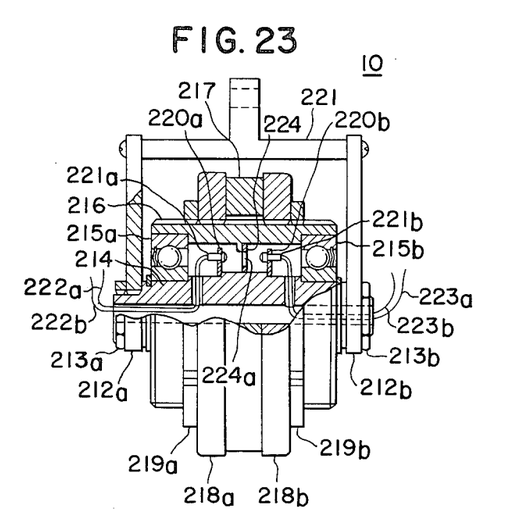
FIG. 23 is a transversal sectional view showing the detail of the distance measuring device utilized in this invention.

FIG. 23 shows the detail of the construction of one example of the distance measuring device 10 shown in FIGS. 5 and 6. It comprises a supporting arm 211 pivotally supported by the carriage 6.

A pair of opposed arms $212_a$ and $212_b$ are secured to the lower end of the supporting arm 211 to support a hollow shaft 214 through nuts $213_a$ and $213_b$. A cylindrical member 216 made of magnetic material is rotatably mounted on the hollow shaft 214. The periphery of the hollow member 216 is provided with screw threads for supporting annular yokes $218_a$ and $218_b$ which clamp therebetween a parmanent magnet 217. Yokes $218_a$ and $218_b$ are made of magnetic material and secured in position by nuts $219_a$ and $219_b$ on the outside thereof.

Annular rings $200_a$ and $202_b$ are mounted on the hollow shaft 214 at an intermediate portion thereof to respectively support opposed luminous element $211_a$ and a light receiving element $21_b$. Lead wires $222_a$, $222_b$, $223_a$ and $223_b$ for supplying power to these elements and for taking out their outputs are led out to the outside through a bore of the hollow shaft 214. An annular ring 224 having slits $224_a$ is interposed between the luminous element and the light receiving element, the number of the slits being determined in accordance with the number of the pulses to be produced. By counting the number of the pulses by a suitable counter, it is possible to measure the running distance of the carriage 6, that is the rolling distance of the yokes $218_a$ and $218_b$.

During operation, the yokes $218_a$ and $218_b$ are attracted by the surface being examined by the flux generated by the permanent magnet 217 and roll as the carriage is moved forwardly or rearwardly. As the yokes $218_a$ and $218_b$ roll, the annular ring 224 secured to the cylindrical member 216 intercepts the light emitted by the luminous element $221_a$ so as to produce pulses of a number corresponding to the number slots $224_a$. Thus, by integrating the number of pulses, the running distance l of the carriage can be determined as follows.

$$l = 2\pi D n / N$$

where D represents the diameter of the yokes, n the number of pulses generated, and N the number of slits $224_a$.

The equation can be calculated by an arithmetic operator connected to the pulse counter.

This distance measuring device has the following advantages.

(1) As the yokes roll along a magnetic surface being examined while the yokes are attracted by the surface so that they can accurately follow the contour of the surface irrespective of any irregularity thus ensuring accurate measuring of the running distance.

(2) The spacing between the yokes is narrower than that between the wheels of the carriage, so that even when the carriage is moved along a wavy path correct measuring of the running distance can be ensured.

(3) As the rotary member 216 is supported on the stationary hollow shaft 214 through ball bearings, it is possible to construct it to have sufficient rigidity.

Although, in this embodiment, a pulse generator comprising paired luminous element and a light receiving element has been shown, it is also possible to use a reversible detector comprising two pairs of luminous elements and light receiving elements, an encorder displaying absolute coordinates, a tachometer generator which detects the number of revolutions, or a number of revolution detector including a cam and a limit switch.

As above described, the nondestructive examining apparatus of this invention can examine narrow portions having complicated configuration, can visually observe the type of the defects, and can analyze and record the detected defect.

What is claimed is:

1. A nondestructive examining apparatus comprising a carriage capable of running along a surface to be examined; an industrial television camera, a profile sensor for profiling the contour of a surface to be examined, and a nondestructive examining unit which are mounted on an arm supported on said carriage; control means for controlling said carriage, said industrial television camera, said profile sensor, and said nondestructive examining unit; and, recording means for recording data produced by said nondestructive examining unit as a result of operation thereof and video images produced by said television camera.

2. The nondestructive examining apparatus according to claim 1 which further comprises a distance measuring device including an arm with one end rotatably connected to said carriage, a hollow shaft supported by a lower end of said arm, a magnet roller rotatably mounted on said shaft, said magnet roller rolling along a surface to be examined while being held in contact therewith by magnetic force and means for counting the number of revolutions of said magnet roller.

3. The nondestructive examining apparatus according to claim 1 wherein said nondestructive examining unit comprises a parallelogram, an outer member swingably pivoted to one end of said parallelogram, in inner member for supporting a probe, means for supporting said inner member to be swingable in a direction perpendicular to the direction of swinging of said outer member, and means for oscillating the end of said parallelogram.

4. The nondestructive examining apparatus according to claim 1 further comprising means for controlling the position of said arm in accordance with the profile sensed by said profile sensor.

5. The nondestructive examining apparatus according to claim 1 wherein said nondestructive examining unit comprises a magnetic core disposed close to a body to be examined, an inductor coil would about said core for producing magnetic flux through said core and through said body thereby inducing eddy current in said body, and means to detect impedance variation of said inductor coil caused by the presence or absence of a defect in said body.

6. The nondestructive examining apparatus according to claim 5 wherein said counting means is contained in a space between said hollow shaft and said magnet roller and comprises an annular ring provided with a plurality of circumferentially spaced slits, and a luminous element and a light receiving element which are disposed on the opposite sides of said annular ring.

7. A nondestructive examining apparatus comprising an industrial television camera carried by a carriage movable along a surface to be examined, said camera including means for changing a field of view, means for adjusting a focal length of said camera, and an illuminating lamp; a monitor television for displaying image signals produced by said industrial television camera; means for inputting data characters; means for synthesizing data regarding a position of said field of view of said television camera, a position of said carriage, a position of an arm swingably mounted on said carriage for supporting said industrial television camera, said video signals and said inputted data characters to obtain a synthesized data signal, a monitor television for displaying said synthesized data signal, a nondestructive examining unit carried by said carriage to contact a surface to be examined; and means for recording picture images displayed on said monitor television and an output of said nondestructive examining unit.

8. The nondestructive examining apparatus according to claim 1 or 7 wherein said nondestructive examining unit comprises at least a pair of rotatable magnets and means for urging said magnets to contact against a surface to be examined.

9. The nondestructive examining apparatus according to claim 8 wherein said carriage comprises a pair of opposed elongated frames, means for pivotably coupling together said frames at an intermediate point thereof, and wherein said pair of magnets are rotatably carried by opposite ends of each one of said frames.

* * * * *